United States Patent
Amend et al.

(10) Patent No.: US 7,414,255 B1
(45) Date of Patent: Aug. 19, 2008

(54) DROP COUNTER

(76) Inventors: John R. Amend, 2135 Baxter Dr., Bozeman, MT (US) 59715; Dale A. Hammond, 55-705 Wahinepee St., Laie, HI (US) 96762; Richard A. Hermens, 1602 Gekeler La., LaGrande, OR (US) 96762; W. Alexander Whitla, 6 Morgan La., Sackville, New Brunswick (CA) E4L 4E3

( * ) Notice: Subject to any disclaimer, the term of this patent is extended or adjusted under 35 U.S.C. 154(b) by 0 days.

(21) Appl. No.: 11/390,483

(22) Filed: Mar. 27, 2006

Related U.S. Application Data

(60) Provisional application No. 60/665,651, filed on Mar. 25, 2005.

(51) Int. Cl.
- G01N 15/06 (2006.01)
- G01N 21/85 (2006.01)
- G01F 1/712 (2006.01)
- A61M 31/00 (2006.01)

(52) U.S. Cl. .................. 250/573; 250/574; 356/410; 73/861.06; 604/65

(58) Field of Classification Search .............. 250/573, 250/559.32, 222.2, 224, 574, 564, 565; 356/436, 356/410, 427, 335–343, 411, 441, 442; 359/228, 359/40, 41, 253, 272; 73/170.17, 861.06, 73/861.41; 604/65, 251, 507
See application file for complete search history.

(56) References Cited

U.S. PATENT DOCUMENTS

| | | | |
|---|---|---|---|
| 3,563,090 A | 2/1971 | Deltour | |
| 3,734,622 A * | 5/1973 | Adler | 356/338 |
| 4,181,130 A | 1/1980 | Bailey | |
| 4,314,484 A | 2/1982 | Bowman | |
| 4,509,943 A | 4/1985 | Hanzawa | |
| 4,533,350 A | 8/1985 | Danby et al. | |
| 4,673,820 A * | 6/1987 | Kamen | 250/573 |
| 4,786,800 A | 11/1988 | Kamen | |
| 4,820,281 A | 4/1989 | Lawler, Jr. | |
| 4,936,828 A * | 6/1990 | Chiang | 604/65 |
| 5,045,069 A | 9/1991 | Imparato | |
| 5,152,424 A | 10/1992 | Weinreb et al. | |
| 5,331,309 A | 7/1994 | Sakai | |
| 5,411,052 A | 5/1995 | Murray | |
| 5,982,289 A | 11/1999 | Kingsley et al. | |
| 6,599,282 B2 | 7/2003 | Burko | |

* cited by examiner

*Primary Examiner*—Georgia Y. Epps
*Assistant Examiner*—Don Williams
(74) *Attorney, Agent, or Firm*—Richard C. Conover

(57) ABSTRACT

The present invention relates to a Drop Counter for counting a succession of falling liquid drops. The Drop Counter includes a light emitting diode for providing a light beam directed to a falling liquid drop. A photo diode sensor is positioned in side-by-side relation with the light emitting diode and detects reflected light from the falling liquid drop. The photo diode sensor provides an output signal when reflected light is detected and further includes a counter for receiving the output signal and counting the number of times the output signals are received.

3 Claims, 4 Drawing Sheets

DROP COUNTER

This application claims the benefit of provisional application Ser. No. 60/665,651 filed Mar. 25, 2005.

BACKGROUND OF THE INVENTION

This invention relates to apparatus for counting drops and this particular application for counting drops from a burette to obtain a measure of the amount of liquid reactant (titrant) added to an unknown solution.

Drop counters are known. These drop counters use apparatus directing a light beam across a chamber toward a light sensor on the other side of the chamber. When a drop falls through the chamber the light beam is interrupted, and thus providing an indication of the presence of a drop. See for example U.S. Pat. No. 4,181,130 to Bailey. Other known apparatus include a light source for directing a light beam toward a falling drop and include a beam detector located to detect a refracted light beam that has passed sidewardly out of a drop. See U.S. Pat. No. 5,982,289 to Kingsley, et. al.

There is a need for a compact drop counter which is reliable and not affected by ambient light or by conditions occurring when drops become fragmented.

SUMMARY OF INVENTION

The present invention relates to a Drop Counter for counting a succession of falling liquid drops. The Drop Counter includes a light emitting diode for providing a light beam directed to a falling liquid drop. A photo diode sensor is positioned in side-by-side relation with the light emitting diode and detects reflected light from the falling liquid drop. The photo diode sensor provides an output signal when reflected light is detected and further includes a counter for receiving the output signal and counting the number of times the output signals are received.

BRIEF DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF PREFERRED EMBODIMENTS

Figure 1:
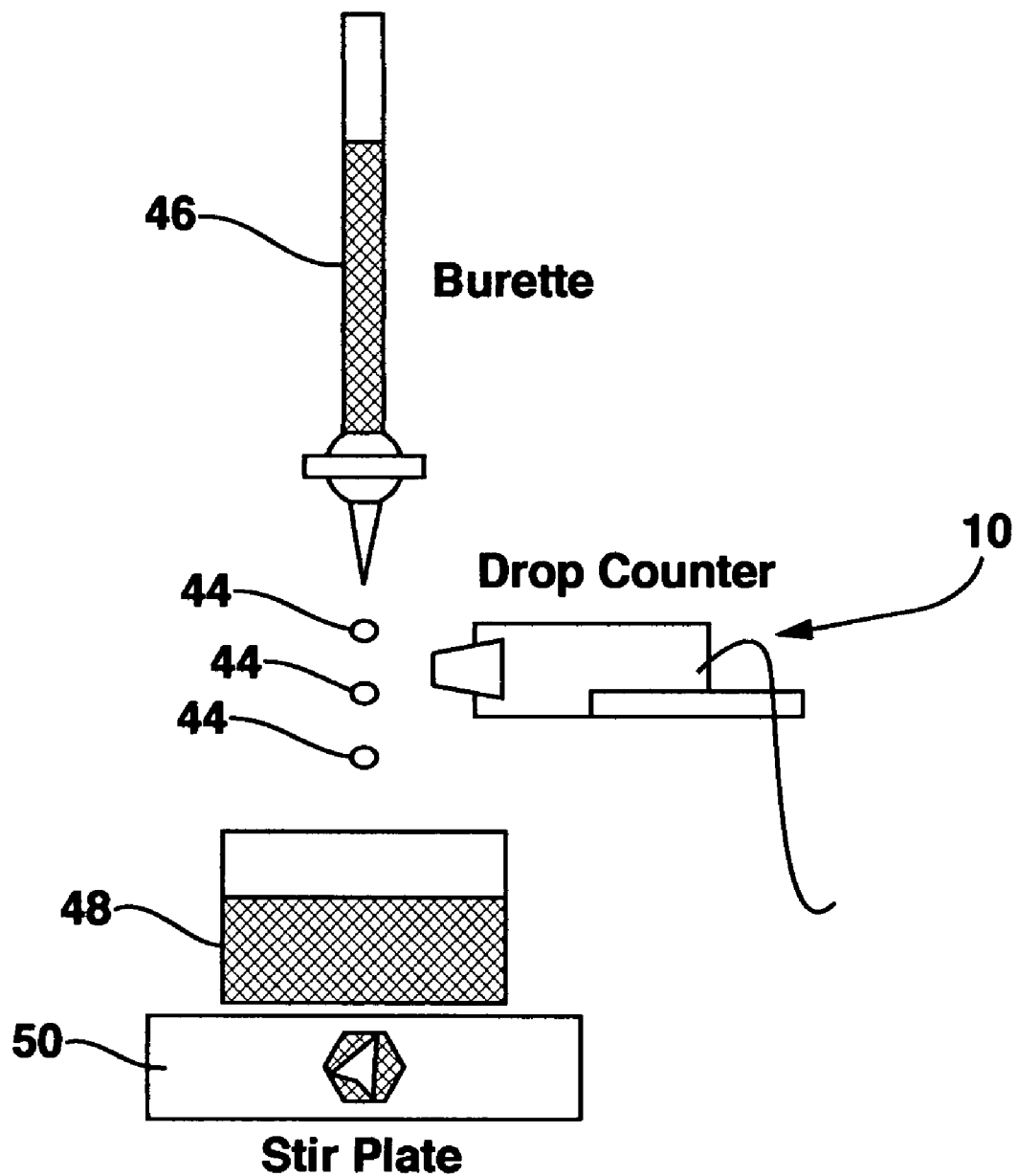
FIG. 1 is a schematic view of a drop counter in accordance with the present invention illustrating the drop counter in operational use.

A common analytical technique used in standard analytical chemical procedures is to determine the volume of titrant added to an unknown solution. This process is called titration. A drop counter 10, as shown in FIG. 1, can provide assistance in measuring the amount of titrant added to this unknown solution.

Figure 3:
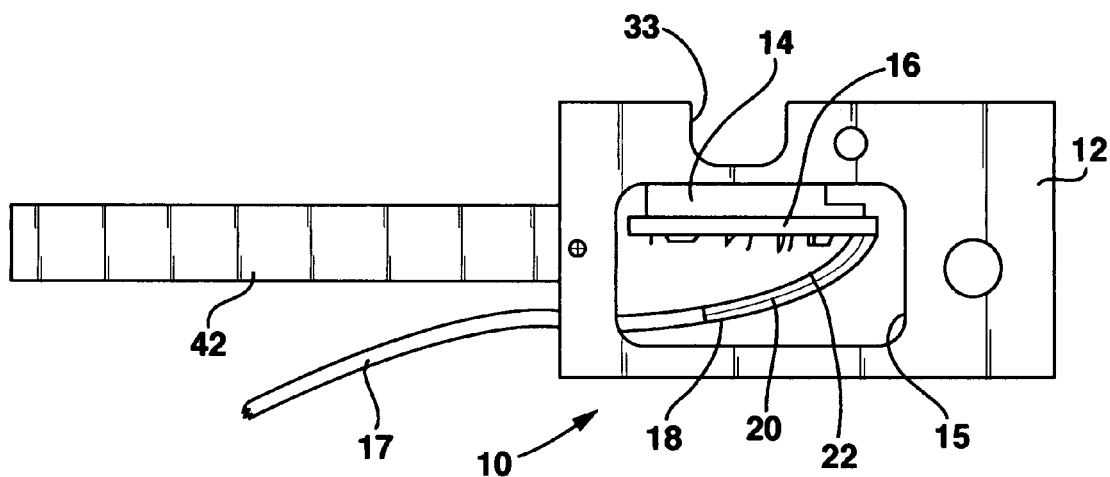
FIG. 3 is a rear plan view of the drop counter shown in FIG. 2.
Figure 4:
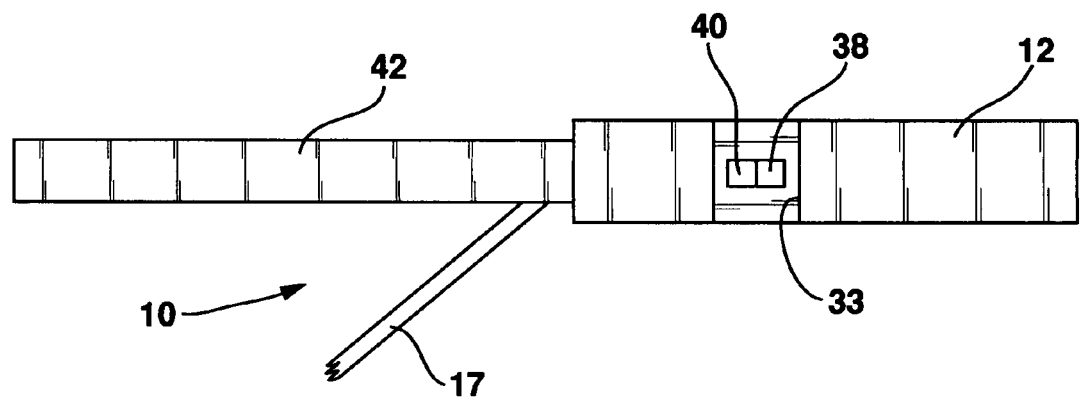
FIG. 4 is a front elevational view of the drop counter shown in FIG. 2.

The drop counter 10 includes a chemically-resistant plastic enclosure 12 for housing a drop sensor 14 and a circuit board 16 in an inset area 15 as shown in FIG. 3. In a preferred embodiment the sensor 14 and circuit board 16 are potted in the enclosure 12 after assembly to make a water-tight assembly.

Figure 5:
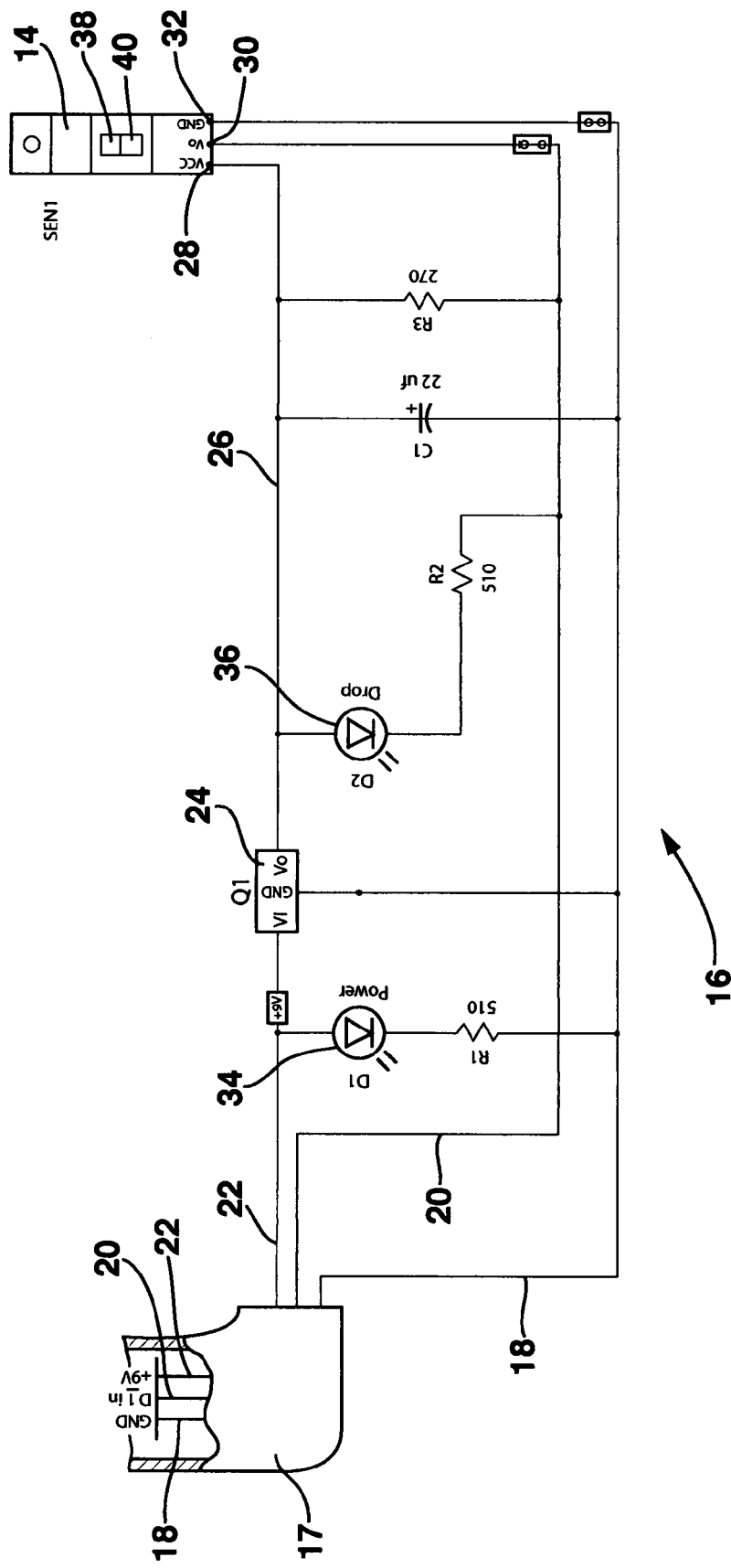
FIG. 5 is a schematic circuit diagram of an electrical circuit used with the drop counter shown in FIGS. 2 and 3.

An electrical schematic of the circuit board 16 is shown in FIG. 5. A conventional CAT-5, eight conductor cable 17 is used to connect the drop counter 10 to lab interface equipment (not shown). The lab interface equipment supplies electrical power to drop counter 10 and interfaces drop counter 10 with a computer where data transmitted via the CAT-5 cable 17 is collected and analyzed. The CAT-5 cable 17 includes a ground lead 18, a data transmission lead 20 and a 9-volt power lead 22. The 9-volt lead 22 is connected to a voltage regulator 24 which converts the 9-volts on lead 22 to 5 volts on lead 26. The lead 26 is connected to the VCC terminal 28 of the sensor 14. The data lead 20 is connected to the Vo terminal on the sensor 14. The ground lead 18 is connected to the GND terminal 32 on the sensor 14.

A green light emitting diode 34 is connected between the power lead 22 and the ground lead 20 to indicate when power is on to the circuit. A red light emitting diode 36 is connected between the 5-volt power lead 26 and the data transmission lead 20 and blinks every time a drop passes the drop counter 10 so as to provide a visual indication of a drop's passage.

In a preferred embodiment, the infrared reflective sensor 14 includes a Sharp Model No. GP2A200LCS, although other reflective sensors could be used equally as well. The sensor 14 includes a cut-out area 33 in which is mounted an infrared light emitting diode 38 which turns "on" and "off" with a 50% duty cycle approximately 8000 times per second. An infrared photo diode sensor 40 is also mounted in cut-out area 33 and senses the light received at its surface. During the "off" cycle of the light emitting diode 38, the infrared sensor 40 measures the ambient light received at its surface. During the "on" cycle, the infrared photo diode 40 again measures the light received at its surface. An electronic circuit within the sensor 14 then subtracts the "off" signal from the "on" signal. If a reflective object is not present the difference is zero and the sensor module 14 produces a logic "1" output. If a reflective object is present within the range of the photo diode 40, (the subtraction "on"–"off") will yield a positive value and the sensor will produce a logic "0" output on the data lead 22. When a logic "0" output appears on the data lead 22, the diode 36 turns on indicating a drop has passed. Because this measurement is repeated approximately 8000 per second, an object need remain in the infrared beam only 150 microseconds for the sensor to record its passage. The subtraction of "off" background light from the "on" cycle measurement effectively makes the sensor immune from changes in background light arriving at the sensor.

Figure 2:
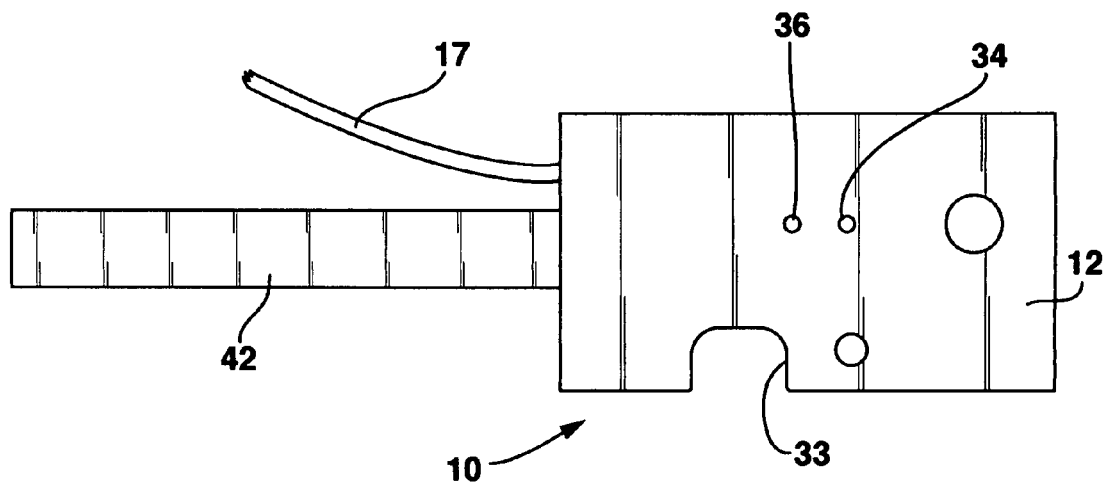
FIG. 2 is a top plan view of a drop counter in accordance with the present invention.

As shown in FIGS. 2 and 3, an elongate support rod 42 has one end fixedly attached to the enclosure 12. The support rod 42 is mounted to the enclosure 12 with a screw 44. The free end of the rod 27 may be mounted to a conventional ring stand (not shown) so as to support the drop counter 10 in a fixed relationship with the stream of drops 44 coming from a burette 46 as best seen in FIG. 1. In operation, a conventional burette 46 is used to provide titrant drops 44 for insertion into an unknown solution 48 as shown in FIG. 1. Unknown solution 48 is often stirred by a conventional stir plate 50 so as to mix thoroughly titrant drops 44 and the unknown solution. Since drops 44 from burette 46 are quite constant in size, knowing the number of drops added to an unknown solution 48 provides a way of calculating the volume of known titrant added to the unknown solution. The rate of drops leaving burette 46, however, does vary considerably as the burette is emptied. But, by counting drops 24, an accurate, instantaneous measure of the volume of titrant delivered may be ascertained.

When counting drops, drops may fragment when they leave the tip of the burette to fall through the air to solution 48. Further, when a drop hits the solution, a splash may occur. Both of these situations may cause the counter to record false counts. To compensate for these two problems, a 20 millisecond "dead time" is created immediately after the presence of a drop is recorded, during which the drop counter is insensitive to pulses generated by sensor 14. This permits both fragmented drops 44 and splashes to fall into the unknown solution before the circuit again becomes sensitive and is ready to count a following, fresh drop. This "dead time" can be created with a 20 millisecond delay in the software of the counting device that is triggered at the arrival of a drop signal. It can also be created with a multi-vibrator circuit through which the sensor's signal is passed to the interface counting circuit.

The output of the drop counter 10 is directed to the lab interface equipment such as a computer via data transmission lead 20 for recording and further processing. By counting drops 24, the amount of titrant supplied to the unknown solution 48 can be calculated.

While the fundamental novel features of the invention have been shown and described, it should be understood that various substitutions, modifications and variations may be made by those skilled in the art without departing from the spirit or scope of the invention. Accordingly, all such modifications or variations are included in the scope of the invention as defined by the following claims.

We claim:

1. A drop counter for counting a succession of falling liquid drops each having an arcuate outer surface comprising:
   a light emitting diode for providing a light beam directed toward the outer surface of the falling liquid drop;
   a photo diode sensor positioned in side-by-side relation with the light emitting diode and facing the falling liquid drops for detecting light reflected when the beam strikes the outer surface of the falling liquid drop;
   the photo diode sensor providing a first output signal when reflected light is detected; and
   means for receiving the first output signal and providing an indication that the photo diode sensor has detected reflected light.

2. A drop counter for counting a succession of falling liquid drops comprising:
   a light emitting diode for providing a light beam directed to a falling liquid drop;
   means for repetitively turning the light emitting diode "on" and "off";
   a photo diode sensor positioned in side-by-side relation with the light emitting diode for detecting light and providing a first output signal which is an aggregate of reflected light received from the falling liquid drop and ambient light during the "on" cycle and providing a second output signal corresponding to the ambient light during the "off" cycle;
   an electronic circuit for subtracting the second output signal from the first output signal and producing a logic "1" output signal if the difference is zero and providing a logic "0" output signal if the difference is positive;
   means for receiving the logic output signals and providing an indication that the photo diode sensor has detected reflected light and thus a drop has passed when a logic "0" signal is received; and
   a counting means for counting the number of times a logic "0" signal is received.

3. The drop counter according to claim 2 is further including means for deactivating the counting means for a preselected time period after a logic "0" signal is received.

* * * * *